United States Patent
Pounder et al.

(10) Patent No.: US 6,780,162 B2
(45) Date of Patent: Aug. 24, 2004

(54) CASTING MATERIAL

(75) Inventors: Neill Malcolm Pounder, Wheldrake (GB); Julian Anthony Webb, Colton (GB); Steven David Hutcheon, Bootham (GB)

(73) Assignee: BSN Medical, Inc., Wilmington, DE (US)

( * ) Notice: Subject to any disclaimer, the term of this patent is extended or adjusted under 35 U.S.C. 154(b) by 55 days.

(21) Appl. No.: 09/936,386

(22) PCT Filed: Jan. 9, 2001

(86) PCT No.: PCT/GB01/00068

§ 371 (c)(1),
(2), (4) Date: Jan. 22, 2002

(87) PCT Pub. No.: WO01/51102

PCT Pub. Date: Jul. 19, 2001

(65) Prior Publication Data

US 2002/0161318 A1 Oct. 31, 2002

(30) Foreign Application Priority Data

Jan. 10, 2000 (GB) .............................................. 0000331

(51) Int. Cl.⁷ .................................................... A61F 5/08
(52) U.S. Cl. .............................................. 602/8; 602/6
(58) Field of Search ......................................... 602/6, 8

(56) References Cited

U.S. PATENT DOCUMENTS 5,158,530 A * 10/1992 Conklin

* cited by examiner

Primary Examiner—Nicholas D. Lucchesi
Assistant Examiner—Lalita M. Hamilton
(74) Attorney, Agent, or Firm—Adams Evans P.A.

(57) ABSTRACT

A medical bandaging product having a moisture curable hardening agent and a flexible liquid-permeable braided and/or tubular fabric substrate for casting or splinting, a method of manufacture of such a medical bandaging product, and a bandaging system comprising such a bandaging product within a moisture impervious package with means for resealing the package.

9 Claims, 8 Drawing Sheets

CASTING MATERIAL

This application is a national stage application, according to Chapter I of the Patent Cooperation Treaty. This application claims the priority date of Jan. 10, 2000 for Great Britain Patent Application No. 0000331.9.

BACKGROUND OF THE INVENTION

This invention relates to the field of orthopaedic medicine and more specifically to an improved medical bandage formed of a moisture curable resin and a flexible permeable substrate, a method of manufacture of such a medical bandaging product, and a bandaging system comprising such a bandage within a moisture impervious package with means for resealing the package against entry of moisture.

Medical bandages for use in the treatment of injuries, such as broken bones requiring immobilisation of a body part, are generally formed from a strip of fabric or scrim material impregnated with a substance that hardens into a rigid structure after the strip has been wrapped around the body member. The hardening substance traditionally used in carrying out this procedure is Plaster of Paris.

Conventional practice has been to fabricate or splint upon an injured limb by initially applying to the limb a protective covering of a cotton fabric or the like and then overwrapping the covering and limb with a woven cloth impregnated with Plaster of Paris which has been wetted by dipping in water immediately prior to application. This is still in widespread use but possesses several significant disadvantages. For example, the above described application procedure is messy and time consuming. Several components are required and considerable skill is necessary.

In order to alleviate the above-recited disadvantages of the application procedure for Plaster of Paris casts and splints, unitary splinting materials have been devised and are disclosed in, for example, U.S. Pat. Nos. 3,900,024, 3,923,049 and 4,235,228.

All of these patents describe a padding material with a plurality of layers of Plaster of Paris impregnated cloth.

Such unitary splinting materials are not as messy and can be applied more quickly but still suffer from a number of disadvantages inherent in Plaster of Paris materials.

All Plaster of Paris splints have a relatively low strength to weight ratio, which results in a finished splint that is very heavy and bulky.

Plaster of Paris splints are slow to harden, requiring 24 to 72 hours to reach maximum strength. Since Plaster of Paris breaks down in water, bathing and showering are difficult.

Even if wetting due to these causes can be avoided, perspiration over an extended period can break down the Plaster of Paris and create a significant problem with odour and itching.

A significant advance in the art of casting and splinting is disclosed in U.S. Pat. Nos. 4,411,262 and 4,502,479.

The casting materials disclosed in these patents comprise a flexible fabric impregnated with a moisture curing resin enclosed in a moisture free, moisture impervious package.

Compared to Plaster of Paris, these products are extremely lightweight, have a very high strength to weight ratio and can be made relatively porous, permitting a flow of air through the casting material.

Prior art moisture curing systems included a package within which is contained a plurality of layers of fabric, such as fibreglass, impregnated with a moisture curing resin.

No provision is made for re-closing the package, so that the entire material must be very quickly used after removal from the package since such moisture curing resins will cure in a relatively short period due merely to contact with atmospheric moisture.

This technology has permitted the development of lightweight, easy to apply splints, as exemplified in U.S. Pat. Nos. 4,770,299, 4,869,049, 4,899,738, 5,003,970 and 5,415,622. Such splints now dominate the market for medical splints.

However, known fabrics have the disadvantage that, if the fabric, e.g. fibreglass, is cut this may leave cut fibres and yarns projecting from the splinting material.

As manufactured, this fabric is relatively soft and flexible, and has relatively good conformability. Moreover, the substrate is fully enclosed with the surrounding padding material.

After curing, however, the cut fibres and yarns become hard and needle-like. These projections can project through the thickness of the padding material into contact with the skin of the patient causing skin-sticks, cuts, irritation and itching.

Moreover, the splinting manufacturing process utilising flat fabric is relatively labour intensive since the fabric must be overlaid with other layers of fabric, usually 4 to 8, to produce the substrate. In order to properly form the substrate, the overlaid layers must be carefully aligned so that the width and thickness are even.

In instances where the multiple overlaid layers are stitched together, even more labour is required. Such multi-layered fabrics tend to be bulky and may require a high proportion of resin, further adding to the weight of the finished product. Several layers can mean the product is difficult to handle, whereby each additional layer may reduce flexibility.

Most fabrics used for the substrates of casting and splinting materials are knitted fabrics, as these are inexpensive and readily available. However, knitted fabrics have the disadvantage that there may be limited width-ways conformability Knitted products may also suffer from the disadvantage of having limited torsional stiffness and directionally specific properties, which can be important for the treatment of specific injuries.

Linear fabrics of knitted orthopaedic products often require a relatively large amount of hardening agent, typically 40% by weight of the total weight.

From the above discussion, it can be seen that both the conventional Plaster of Paris casting method and the more recent moisture curable resin casting method possess both advantages and disadvantages.

On the one hand, Plaster of Paris casts are bulky, heavy and difficult to apply whereas moisture curable resin casts are lightweight, durable and relatively easy to apply.

Plaster of Paris can be very easily stored and used as needed since it has a relatively long shelf life so long as it is not completely wetted.

On the other hand, the moisture curable resins are very sensitive to the presence of even minute amounts of moisture, which requires that either the material be packaged in a wide variety of different shapes and sizes or unused portions be discarded, generating a substantial amount of waste and increasing the effective cost of the product.

BRIEF SUMMARY OF THE INVENTION

Therefore, it is an object of the present invention to provide a bandaging product that has a substrate that is uniform in dimension without the requirement for additional fabrication steps after formation of the substrate.

It is an object of the invention to provide a bandaging product that has a braided or tubular substrate that does not require additional layers for strength.

It is an object of the invention to provide a bandaging product that utilises a tubular braided fabric structure as a bandaging substrate.

It is also an object of the invention to provide a bandaging product that combines the advantages of both Plaster of Paris and moisture curable resin systems while avoiding their respective disadvantages.

Thus, according to a first aspect of the present invention there is provided a medical bandaging product having a moisture curable hardening agent and a flexible liquid-permeable substrate wherein the flexible liquid permeable substrate is a braided and/or tubular fabric.

In one embodiment, the substrate will carry the hardening agent in and/or on its structure, ready for easy curing and application.

Surprisingly it has been found that the use of a braided and/or tubular fabric for the flexible permeable substrate of a bandaging product gave a product that prior to curing or hardening is easy to handle with good conformability but which after curing gives a rigid strong orthopaedic product.

This gives an orthopaedic product, such as a casting or splinting product that is stronger and wears better against abrasions, than the casts of the prior art for similar weight of products. The bandaging products of the present invention therefore have a longer useful life as an orthopaedic cast or splint.

Having a stronger cast as described by the present invention also allows less hardening agent to be used to cure and harden the bandaging product, thus being cheaper and easier to manufacture.

Using less hardening agent and layers of fabric for a bandaging product as described in the present invention also gives a lighter product that may still have the required strength needed for an orthopaedic cast or splint.

Having less hardening agent to cure also gives a reduced exotherm, the heat produced on curing which may be uncomfortable to the user.

In one embodiment, the substrate will be braided.

It has surprisingly been found that the braided and/or tubular structure has enhanced physical properties including added strength and enhanced torsional rigidity.

According to a second aspect of the present invention there is provided a method of manufacture of a medical bandaging product carrying a moisture curable agent comprising the step of applying a moisture curable agent to a braided and/or tubular substrate. In one embodiment, the substrate will be braided.

The last object of the invention (to provide a bandaging product that combines the advantages of both Plaster of Paris and moisture curable resin systems while avoiding their respective disadvantages) is accomplished by providing a unitary splinting system with improved strength and convenience.

Thus, in a third aspect of the present invention there is provided a bandaging system comprising a bandaging product comprising a moisture curable agent in and/or on a substrate within a moisture impervious package with means for resealing the package against entry of moisture after a desired length of bandaging product has been removed for use.

In this manner, hardening of the bandaging product remaining in the moisture impervious package is prevented thereby increasing the cost effectiveness of the system.

In one embodiment of the third aspect of the present invention there is provided a bandaging system comprising a bandaging product comprising a moisture curable agent in and/or on a substrate that is braided and/or tubular.

The braided and/or tubular fabric of the substrate comprised in a bandaging product may be provided in several significantly advantageous embodiments. For example, it may be a non-tubular braid, e.g. a webbing strap, formed as a length of flat braided material.

It may alternatively be a tube seamed from a length of flat material that is looped around and suitably attached to form a tubular structure of the present invention, preferably with the raw ends of the flat positioned on the inside of the tube.

The material that is looped around and suitably attached to form a tubular structure of the present invention may be braided.

The braided and/or tubular fabric of the substrate comprised in a bandaging product may be made of any suitable fibres or yarns or combinations thereof.

Suitable fibres include polyester fibres, carbon fibres and jute although any natural or synthetic fibre that can be spun into a suitable yarn or monofilament material and braided may be used.

It is envisaged that in a preferred embodiment that the braided and/or tubular fabric will contain glass fibres.

Resilient fibre such as elastomers e.g. polypropylene fibres can also be used, whether alone or in combination with other fibres, to enhance to give desired properties such as extensibility and impact resistance.

The structure of the braided and/or tubular substrate may be initially manufactured as a braided and/or tubular structure or may first be manufactured as a flat, optionally braided material that is looped around and suitably attached to form the braided and/or tubular structure of the present invention.

Preferably, the braided and/or tubular substrate is manufactured initially as a braided and/or tubular structure ready for use in the present invention, e.g. formed of a suitable fibre such as fibreglass into a webbing strap, formed as a length of flat braided material on a braiding machine, or into length of braided tube on a circular braiding machine.

Embodiments of the present invention may have the fibres nominally at +/−45 degrees to each other thus offering excellent torsional rigidity.

The angle of the fibres of the braid may vary, offering a wide range of different torsional rigidity properties.

The stretch of the material, whether width ways or lengthways will vary the angle of the fibres relative to each other.

It is envisaged that when the braided and/or tubular substrate is stretched lengthways the fibres will run along the lengthways direction at a smaller angle from the lengthways axis then when the braided and/or tubular substrate is stretched widthways.

When the angle of the fibres running lengthways is small when measured from the lengthways axis the substrate has greater lengthways strength than when the angle is large.

Likewise, when the angle of the fibre running widthways is small when measured from the widthways axis the substrate has greater widthways strength than when the angle is small.

Further variations of torsional rigidity may be possible by the inclusion of unidirectional fibres.

These fibres can be laid lengthways or widthways depending on the desired effect required. Such fibres may be elastic fibres.

In short, it is the fibre orientation that gives different structural properties, for instance torsional rigidity, to the braided and/or tubular substrate.

The present invention allows easy changing of the fibre orientation thus enabling a wide range of different rigidity properties of the substrate.

The moisture curable hardening agent used with the bandage of the present invention may be any suitable agent that when cured hardens the bandage to form the orthopaedic support product. A number of commercially available hardening agents are widely available including Plaster of Paris and synthetic resins.

Suitable hardening agents include water curable synthetic resins for casting or splinting products, such as urethane resins formed from the reaction of a polyol with an excess of polyisocyanate (as disclosed in patent applications GB 2092606 A and WO 86/01397). Other suitable agents include an alkoxy silane terminated prepolymer (disclosed in WO96/23531) or an acrylic terminated prepolymer.

These are stronger and wear better against abrasions, than the casts from similar weight products.

The hardening agent may be applied separately to the substrate prior to curing, or the substrate may carry the hardening agent. In a preferred embodiment, the substrate will carry the hardening agent ready for easy curing and application.

Having a bandaging product whereby the substrate carries the hardening agent helps ensure even distribution of the hardening agent throughout the substrate.

Suitably the hardening agent will be coated evenly on the substrate and may typically have a hardening agent coating of around 20% of the total weight of the product.

The braided and/or tubular structure also enables the finished product to have a variety of different thicknesses. In different circumstances a thick, or thin, bandage may be required and the braided and/or tubular structure may be shaped accordingly.

The thickness of the structure may offer different strength and stiffness properties, which according to what is required the appropriate thickness can be chosen.

Suitable a methods of applying a moisture curable agent to a braided and/or tubular substrate include conventional methods of applying a moisture curable agent to a similar substrate for casting or splinting products, such as nip coating and impregnation.

In one embodiment, the substrate will be braided and such methods of applying a moisture curable agent to a braided and/or tubular substrate include conventional methods for casting or splinting products, such as nip coating and impregnation.

In use the braided and/or tubular substrate may, optionally, be pulled over a core of, for example, foam or COREMAT™, (COREMAT is a Trade Mark of British Vita) to give extra strength or stiffness to the structure.

Different sized cores may be used to give a product of various strengths and stiffness as well as thickness.

The core may be supplied in place, within the braided and/or tubular braid and ready for use, or may be supplied separately.

In embodiments where a core is to be used, the width of core may be predetermined in order to determine the correct stretch required of the braided and/or tubular bandage to have the desired torsional rigidity property. Different predetermined widths of core may be used for different torsional rigidity properties.

Different braids, or different designs of braids, may be used to give different properties to the braided and/or tubular structure.

For instance, if enhanced properties are required along the length of the product, unidirectional fibres can be laid down. If the torsional properties are less important, a wider braid can be used and pulled to bring the fibres closer to unidirectional.

It is envisaged that the bandaging product of the present invention will be suitably stored in a container prior to use.

The container used to store the bandaging product of the present invention may be made from any tough durable tear resistant material that will not tear or rip during rough handling, but preferably which can be easily opened by hand. Preferably, this material should be impervious to liquid and gas.

Such materials may be metallic foil or plastics e.g. polyethylene or the like, or laminates thereof.

In the third aspect of the present invention, the container protecting the bandaging product will be resealable so that the entire bandaging product is not required to be used at once.

A suitable resealing means will be employed to reseal the container of the bandaging product.

The container protecting the bandaging product will often comprise a moisture free, moisture impervious package that is resealable, so that the entire bandaging product is not required to be used at once.

Suitable materials and properties for the resealable container protecting the bandaging product will be as described by way of example only with reference to a general container protecting the bandaging product above.

As described, it may be of metallic foil or plastics e.g. polyethylene or the like, or laminates thereof.

By way of example only, the container protecting the bandaging product will often comprise a moisture free, moisture impervious enlarged product storage package, which is integral and communicates with one end of a dispensing sleeve, through which the medical bandaging product in the container is dispensed.

A coil of the medical bandaging product is positioned in the package and the elongate dispensing sleeve may fit snugly around the running end of the medical bandaging product.

The farther end of the dispensing sleeve is openable, but resealable, so that the entire bandaging product is not required to be used at once.

The medical bandaging product may be coiled into a relatively tight coil that limits exposure to air of the medical bandaging product remaining in the container.

The snug fit of the elongate dispensing sleeve around the running end of the medical bandaging product also limits exposure to air of the medical bandaging product remaining in the container.

When the end is properly sealed, the container is sufficiently airtight so that the medical bandaging product remains in its soft, uncured state for much longer that the usual length of time needed to exhaust the supply of medical bandaging product in the container.

If a short length of the medical bandaging product adjacent to the opening should happen to harden, it can be cut away and discarded.

A suitable resealing means will be employed to reseal the interior of container securely against intrusion of moisture, e.g. heat-sealing, or a clamp of any suitable type, such as a scissors type clamp.

Other types of sealing mechanisms are possible such as, for example, a soft, conformable gasket device with spring loaded compression, or a "zip-lock" type integrally formed zipper of a type typical on sandwich bags and other food storage bags, moisture proof tape, or a screw action of sufficient strength to prevent entry of moisture into the sleeve.

One particular suitable device is a pair of spring loaded rollers which as compression takes place rolls slightly backwards, pushing the medical bandaging product back slightly into the sleeve to permit a better seal.

BRIEF DESCRIPTION OF THE DRAWINGS

The invention will now be described by way of example only with reference to the accompanying drawings.

DETAILED DESCRIPTION OF THE INVENTION

Figure 1:
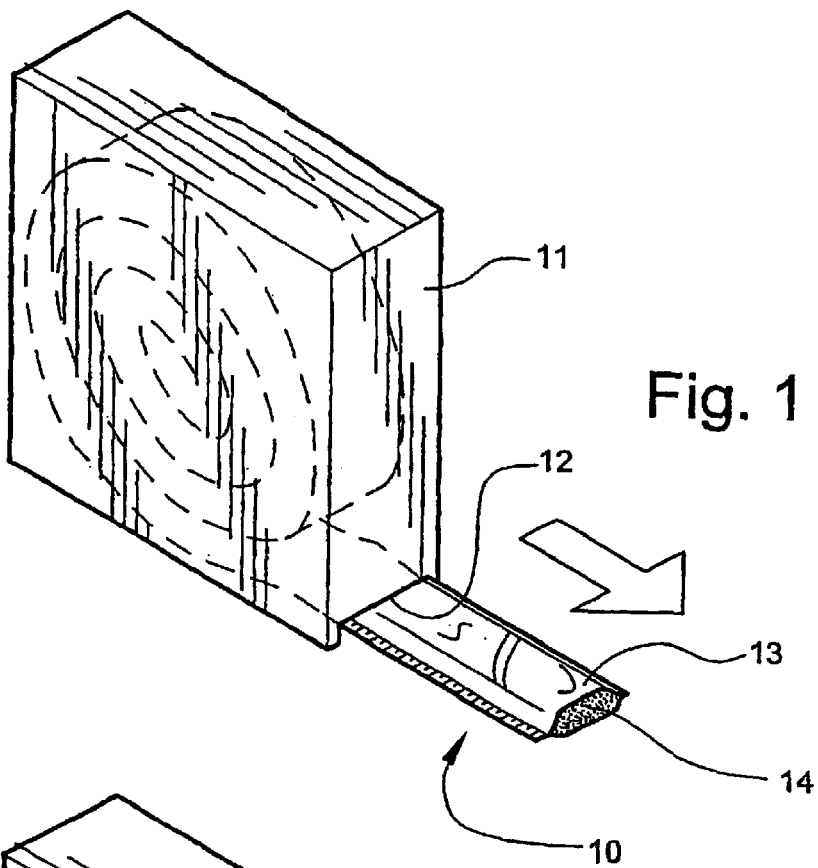
FIG. 1 is a perspective, schematic view showing the medical bandaging product being dispensed from a dispenser.

In FIG. 1 there is shown a medical bandaging product (10) according to the present invention. The medical bandaging product (10) may be sold in any convenient length, such as 7.2 meters, and, for example, is rolled into a coil and positioned in a suitable dispenser carton (11).

The dispenser carton (11) is provided with a slot (12) at one lower corner through which the bandaging product (10) may extend.

The bandaging product (10) is comprised generally of an outer elongate sleeve (13) which is formed of a moisture impervious material, such as two laminated elongated sheets place in registration and heat sealed along its opposite sides to form a tube.

The outer layer is formed of a tear resistant plastic film.

The middle layer comprises aluminium foil and acts as a moisture barrier.

The inner layer is a plastic film having thermoplastic properties suitable for heating-sealing the interior of sleeve (13) securely against moisture.

The sleeve (13) is preferably heat sealed along opposite, parallel extending sides to form an elongate tube.

An elongate medical bandaging product (14), described in detail below, is positioned within the sleeve (13) and is maintained in substantially moisture free conditions until dispensed.

Figure 2:
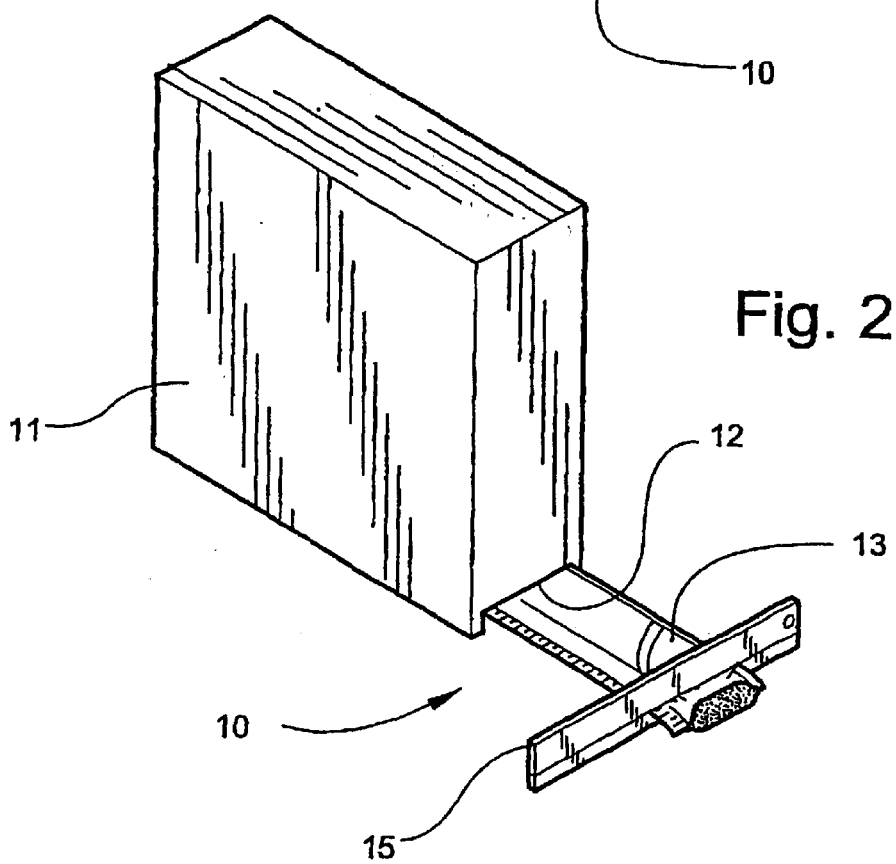
FIG. 2 is a view similar to FIG. 1, showing the unused portion of the medical bandaging product being resealed to prevent entry of moisture.

As is shown in FIG. 2, the end of the sleeve (13) is sealed with sealing means, such as a scissors type clamp (15).

Other types of sealing mechanisms are possible such as, for example, a soft, conformable gasket device with spring loaded compression, moisture proof tape, or screw action of sufficient strength to prevent entry of moisture into the sleeve (13).

One particular suitable device (not shown) is a pair of spring loaded rollers which as compression takes place rolls slightly backwards, pushing the medical bandaging product (14) back slightly into the sleeve (13) to permit a better seal.

Another possible sealing means (not shown) is a device which pushes the medical bandaging product (14) back into the sleeve (13) a sufficient distance (approximately 2.5 cm), so that the open end sleeve (13) may be heat sealed once again.

Figure 3:
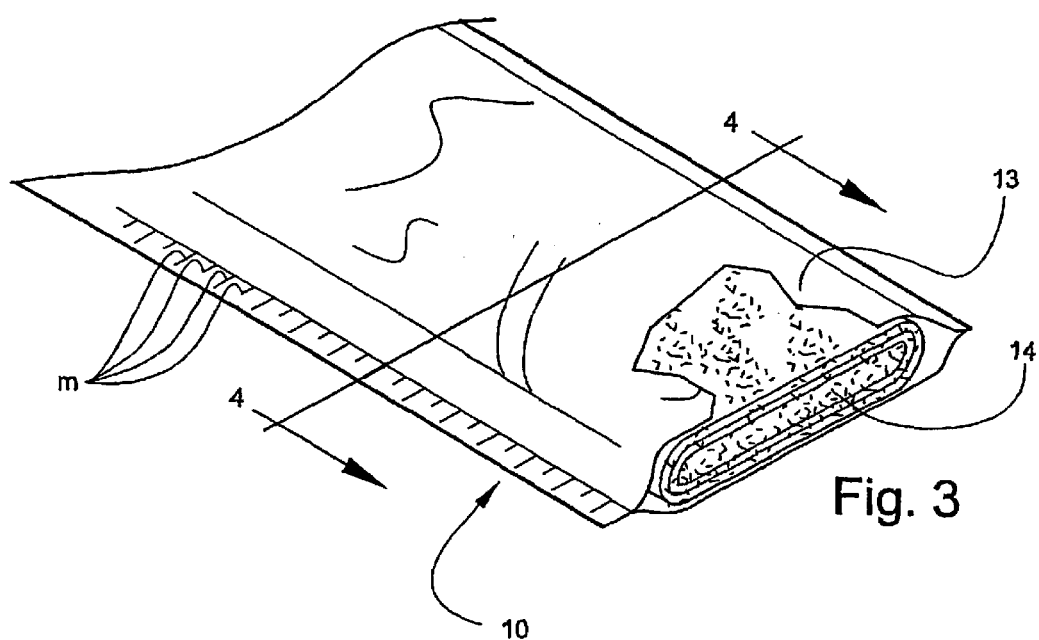
FIG. 3 is a perspective view with parts broken away of a cut length of medical bandaging product.

Since the approximate length of the medical bandaging product (14) is best determined by measurement, measurement marks "M" may be printed on one edge of the sleeve (13) as is best shown in FIG. 3.

Once the appropriate length of medical bandaging product (14) has been dispensed and cut from the roll, it is removed from sleeve (13), it is removed from the sleeve (13) and the sleeve (13) is discarded.

Figure 4:
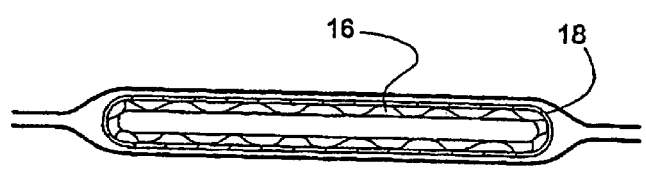
FIG. 4 is a vertical cross-section taken substantially along lines 4—4 of FIG. 3.
Figure 5:
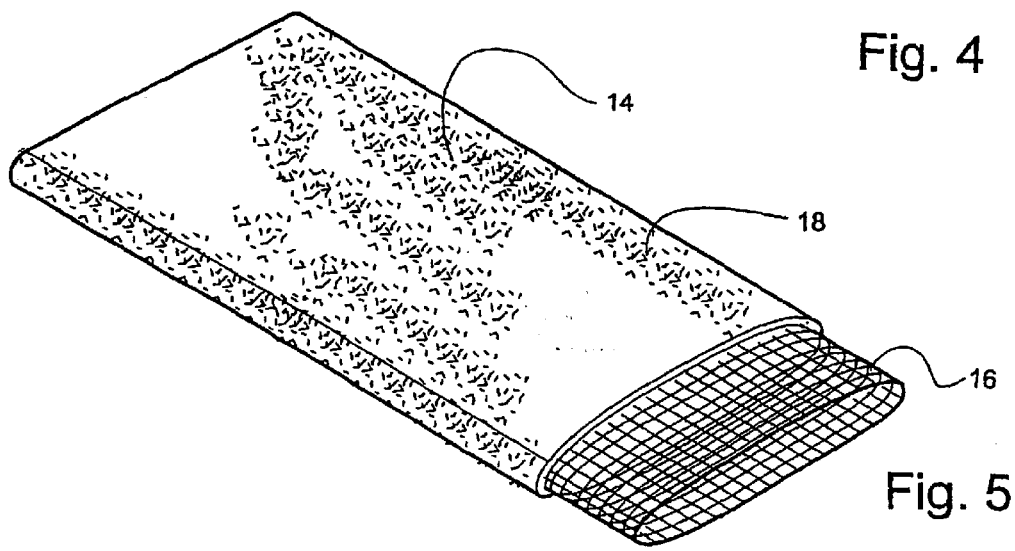
FIG. 5 is a perspective view of a length of the medical bandaging product with the substrate layer exposed for clarity.

Referring now to FIGS. 4 and 5, in another embodiment of the present invention the medical bandaging product (14) comprises a braided tubular substrate (16) which is preferably formed by a braiding yarn formed of a suitable fibre such as fibreglass into a tube on a circular braiding machine enclosed with a length of tubular wrapping (18).

Substrate (16) may alternatively be formed by seaming a length of flat braided material into a tube with the raw ends of the tube positioned on the inside of the tube by turning the tube inside out. However, because of the labour involved in these manufacturing steps, braiding the tube is believed to be the most efficient and cost effective means of forming the substrate.

By braiding the substrate (16), the principal remaining construction step is to cut the braided tube to length so that it is generally corresponds to the length of the sleeve (13) into which the prepared medical bandaging product (14) will be packaged.

The medical bandaging product (14) may be formed in any needed width, for example between 2.5 cm and 20 cm.

One preferred embodiment comprises a 7.5 cm wide medical (14) positioned within a 10 cm wide sleeve (13). In general, the sleeve (13) varies between 7.5 to 25 cm and within that range can accommodate medical bandaging product having widths of 2.5 cm and 20 cm.

Figure 8:
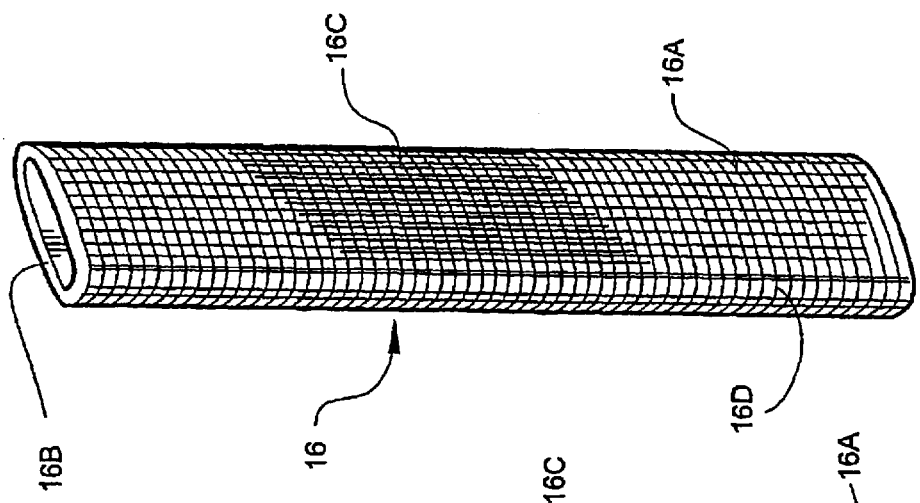
FIG. 8 is a perspective view of the substrate shown in FIG. 7.
Figure 7:
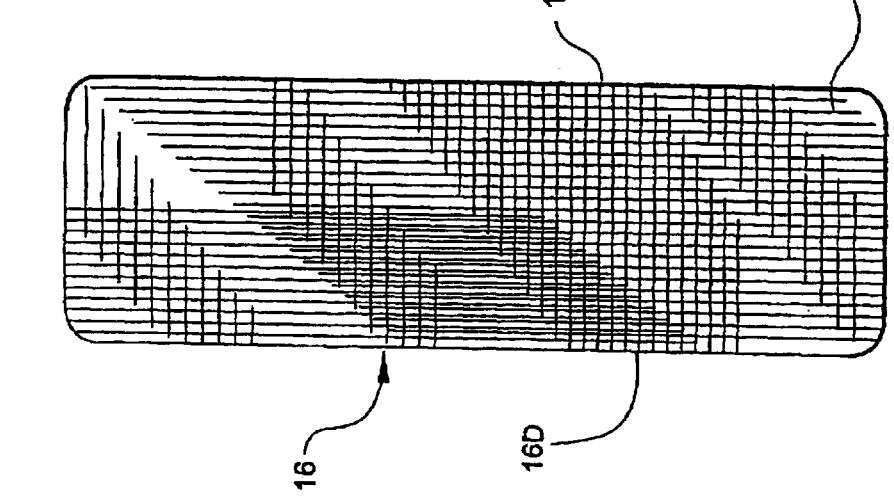
FIG. 7 is a side elevation of the braided tubular knitted substrate in a flattened condition, as it will be incorporated into the medical bandage.
Figure 6:
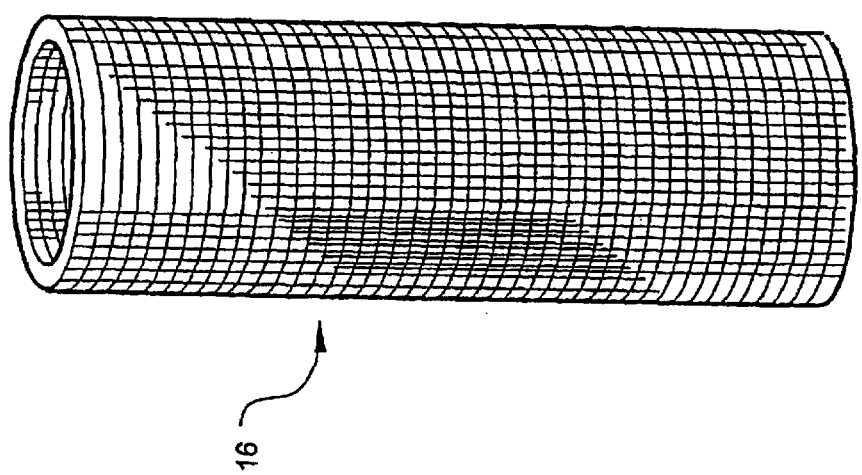
FIG. 6 is a perspective view of a length of braided tubular knitted substrate.

As shown FIGS. 6, 7 and 8, substrate (16) is formed by flattening the braided tube (FIG. 6) to form two major, longitudinally-extended sides (16A), (16B) (FIGS. 7 and 8).

The flattened tube also forms two opposed, folded side edges (16C), (16D) of the substrate (16).

In contrast to prior art constructions, which include raw, cut edges with a multitude of exposed and outwardly projecting yarn and fibre ends, these side edges (16C), (16D) are rounded, smooth, integral and uncut.

Thus, there are no exposed cut ends to harden into sharp, needle like projections when the curing of the moisture resin is completed.

In addition, the substrate is strengthened by the braided tubular layers acting as a double layer, continuous structure.

No sewing is required to align the layers, and the manufacturer has greater control over the width of the medical bandaging product (14).

A short length of the substrate (16) is shown in FIGS. 6, 7 and 8. Ordinarily, the substrate (16) will be in much longer lengths coextensive with the length of the material (14) to be formed.

Figure 9:
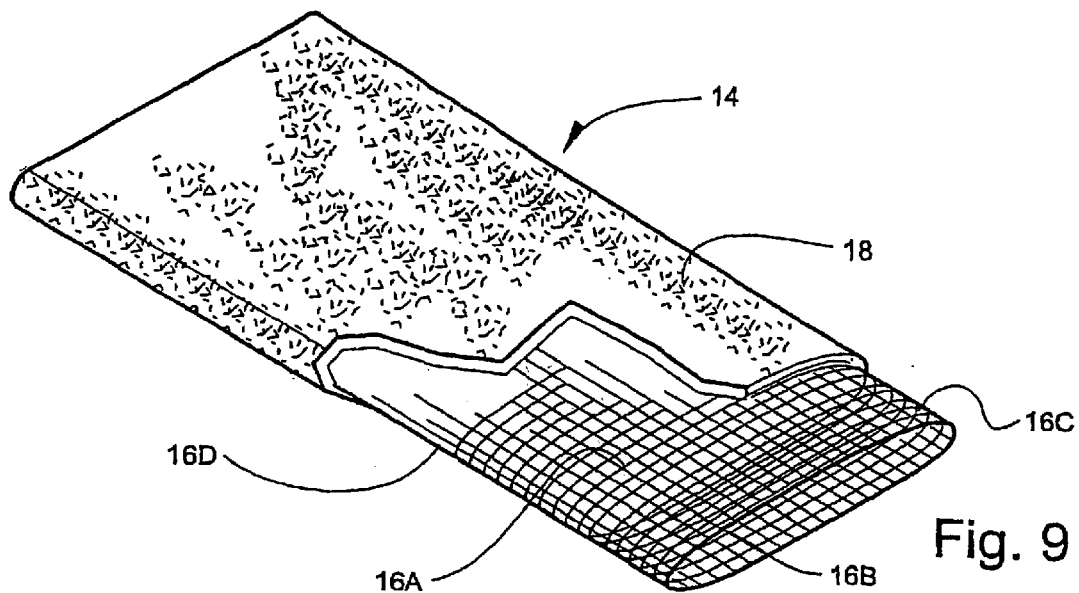
FIG. 9 is a perspective view, with parts broken away, showing the flatted braided tubular substrate positioned in the padding to form the medical bandage.

While cut edges are formed on the ends of the substrate (16) when severed from the length of medical bandaging product (14), these ends can be folded inwardly and/or covered with a double thickness of the braided and/or tubular wrapping (18) (FIG. 9)

The braided tubular wrapping (18) is formed of a soft, flexible non-woven fibre such as polypropylene or some other suitable hydrophobic fibre such as is presently used on Ortho-Glass™ brand synthetic splinting material manufactured by the Casting Division of Smith & Nephew, Inc., this product provides a cushioning protective layer between the skin of the patient and hardened substrate (16).

Substrate (16) is impregnated or coated with a reactive system which remains stable when maintained in substantially moisture free conditions but which hardens upon exposure to sufficient moisture to form a rigid, self supporting structure.

Figure 10:
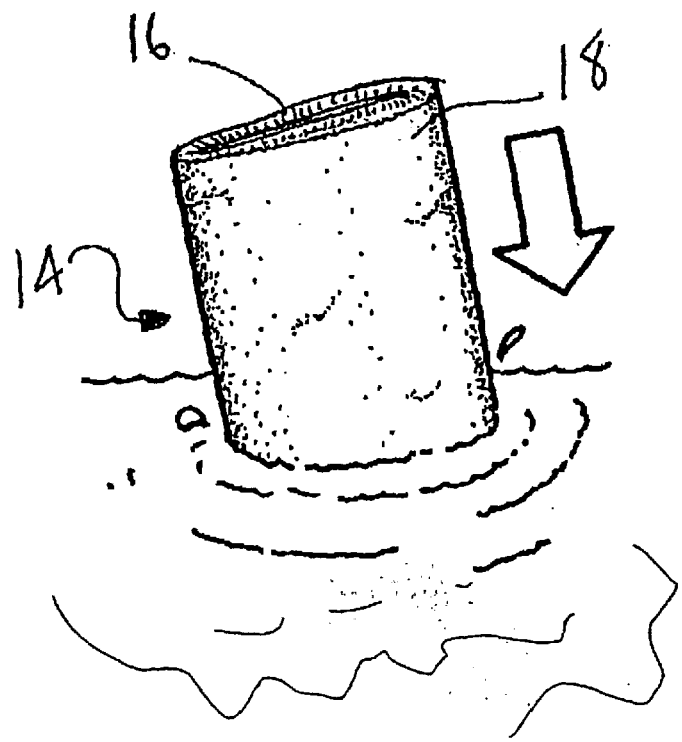
FIG. 10 illustrates the activation of the moisture curable resin by wetting.

As is shown in FIG. 10, moisture curing is activated by dipping the medical bandaging product (14) in water.

Then excess moisture is squeezed from the medical bandaging product (14) by, for example, rolling up in a towel.

Alternatively, moisture curing can take place over a longer period by allowing contact between the reactive system on substrate (16) and atmospheric moisture.

Figure 11:
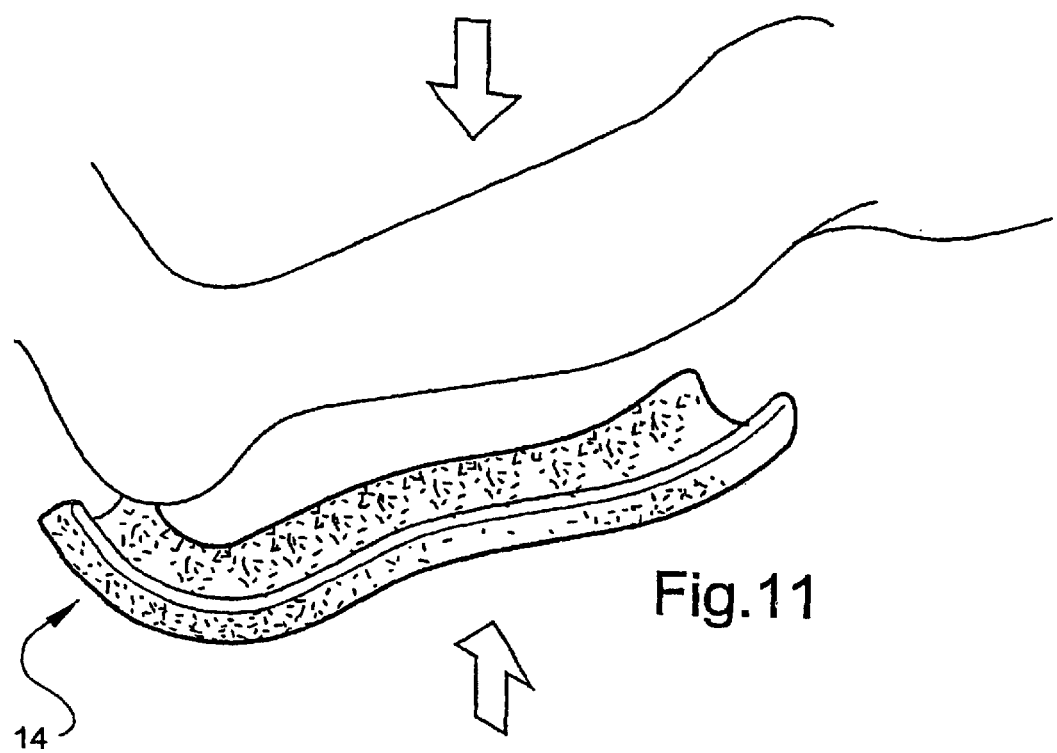
FIG. 11 shows the medical bandaging product after removal from the sleeve being formed to fit the contour of a body member.

Referring now to FIG. 11, an appropriate length of the medical bandaging product (14) is formed to the shape of the body member to be immobilised.

Figure 12:
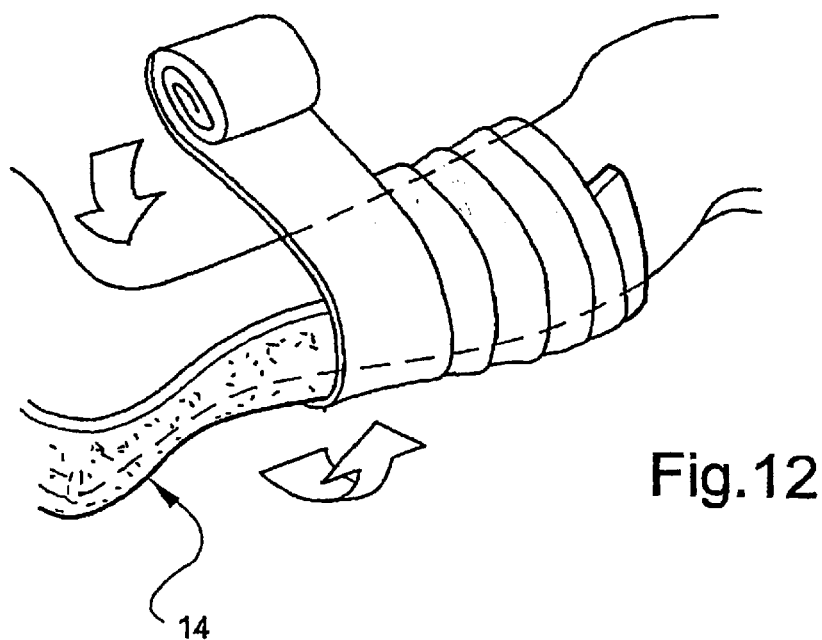
FIG. 12 is a perspective view of the hardening medical bandaging product being secured into place on a body member by means of a covering wrap.

This particular type of splint, known as a posterior short leg splint, is formed by moulding a length of the medical bandaging product (14) to the calf and up over the heel and onto the foot. Then, medical bandaging product (14) is overwrapped with a conventional elastic bandage, as is shown in FIG. 12.

Figure 13:
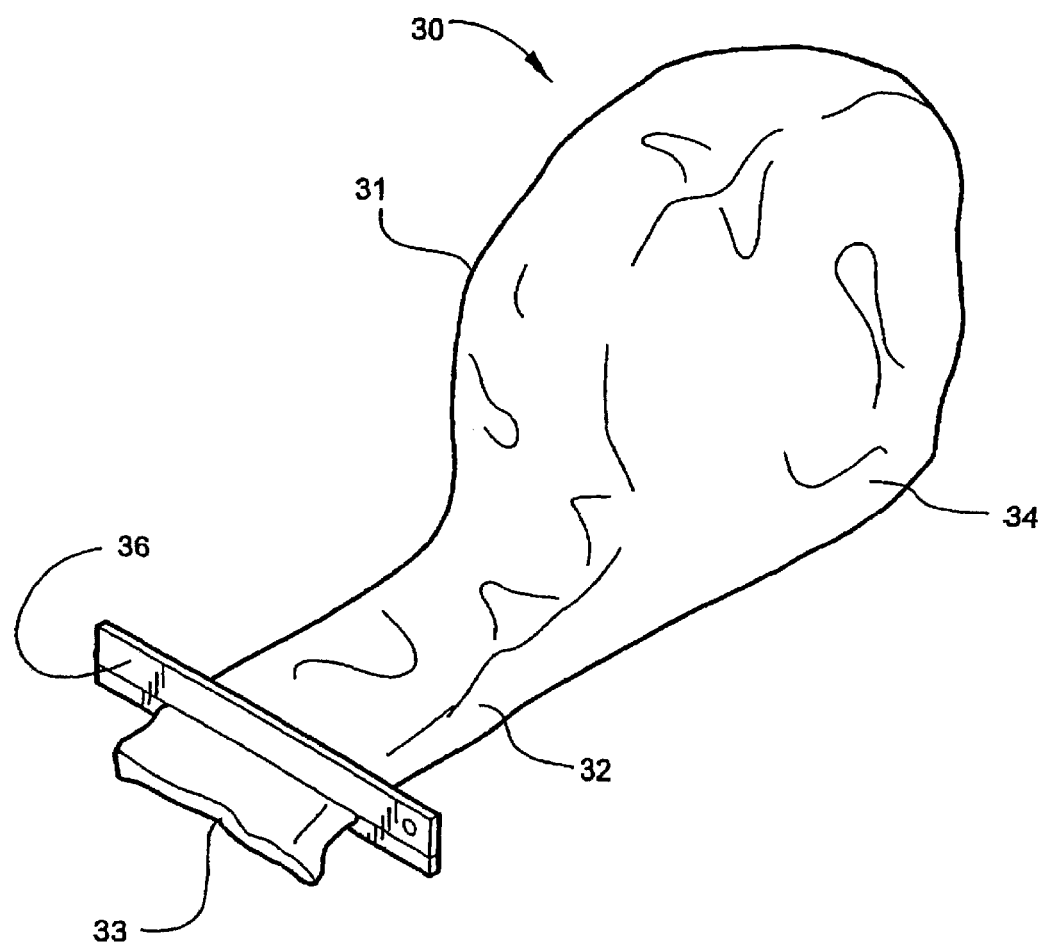
FIG. 13 is a perspective view of a dispensing container for holding the medical bandaging product according to an alternative embodiment.

Referring now to FIG. 13, the medical bandaging product according to another embodiment of the invention is shown at broad reference numeral (30).

The medical bandaging product (14) is positioned within a container (31) which is formed of two laminated sheets placed in register and heat sealed along a common seam to form a moisture proof container of the same material and construction as the sleeve (13).

The outer layer is formed of a tear resistant plastic film and the middle layer comprises an aluminium foil and acts as a moisture barrier.

The inner layer is a plastic film having thermoplastic properties suitable for heat-sealing the interior of container (31) securely against intrusion of moisture.

As is also shown in FIG. 11, container (31) comprises an elongate dispensing sleeve (32) having an openable end (33). Through this, the medical bandaging product (14) in the container (31) is dispensed.

A coil of the medical bandaging product (14) is positioned in an enlarged product storage package (34), which is integral and communicates with dispensing sleeve (32).

The end (33) of dispensing sleeve (32) may be sealed with a clamp (36) of any suitable type, for example, the clamp (36) described above, or a "zip-lock" type integrally formed zipper of a type which is typical on sandwich bags and other food storage bags.

As is shown in FIG. (14), the dispensing sleeve (32) fits snugly around the medical bandaging product (14) in order to limit exposure of the medical bandaging product (14) to air that enters when the opening (33) is not sealed.

Figure 14:
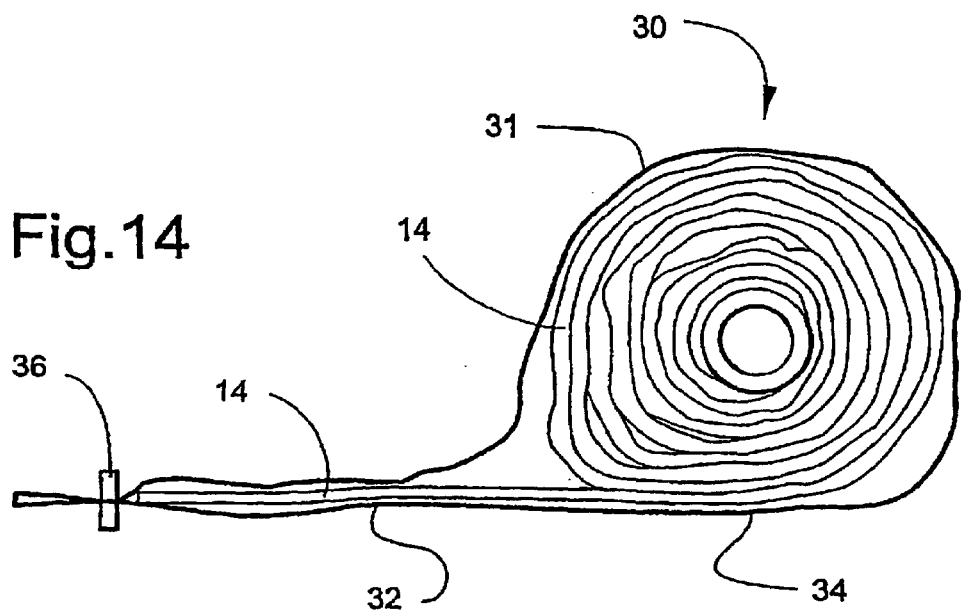
FIG. 14 is a vertical side elevation with partial cross-section of the dispensing container shown in FIG. 13.
Figure 15:
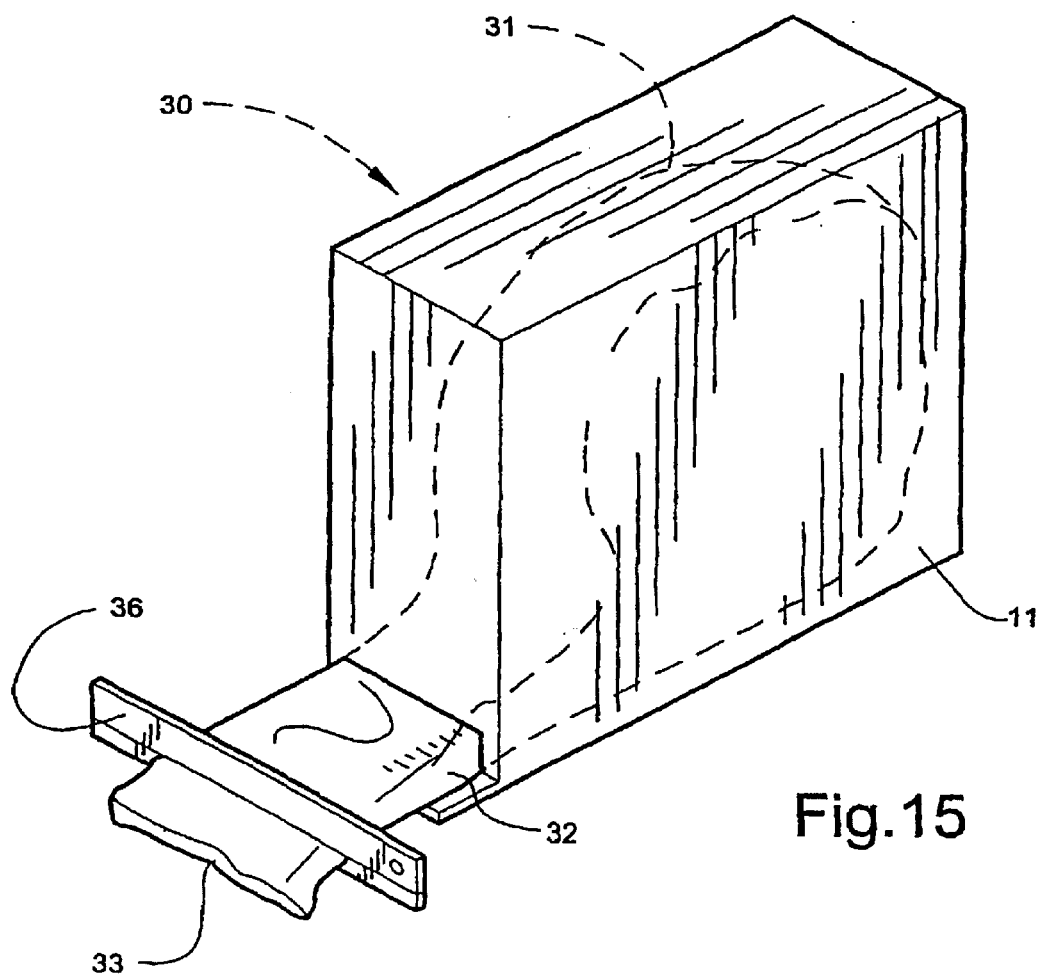
FIG. 15 is a perspective view of a carton into which the dispensing container, also shown, is positioned.

FIG. 14 also illustrates that a desired length of medical bandaging product (14) is dispensed by removing clamp (36) and grasping the exposed end of the medical bandaging product (14).

The appropriate length is pulled out of container (31) the medical bandaging product (14) uncoiling in the storage package (34).

When the proper length has been dispensed through opening (33), it is cut and the end of the material (14) remaining in the container (31) is tucked back into the dispensing sleeve (32). The open end (33) is quickly resealed with the clamp (36).

As shown in FIG. (15), the medical bandaging product (30) can be placed inside a dispensing carton (11), with the dispensing sleeve (32) of container (31) projecting out of the slot in the bottom of carton (11).

Figure 16:
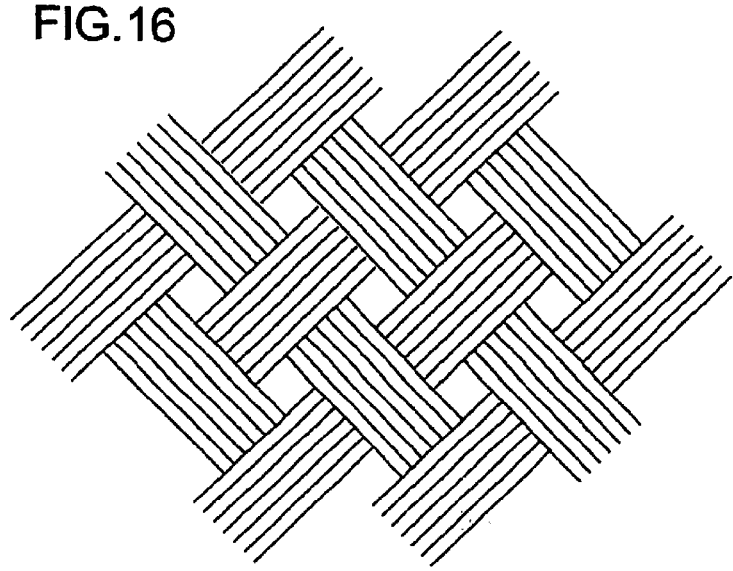
FIG. 16 is a view of the braid fibres or yarns at approximately 45 degrees to each other, and approximately 45 degrees to both the horizontal axis and vertical axis across the bandage.
Figure 17:
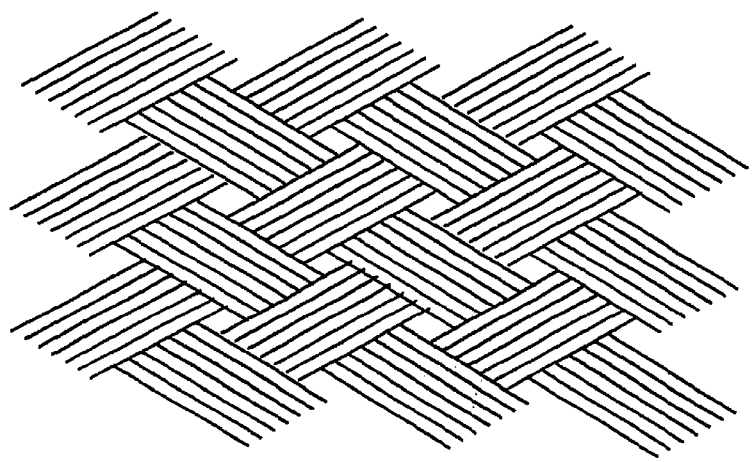
FIG. 17 is a view of the braid fibres or yarns at approximately 30 degrees from the horizontal axis across the bandage and approximately 60 degrees from the vertical axis across the bandage.
Figure 18:
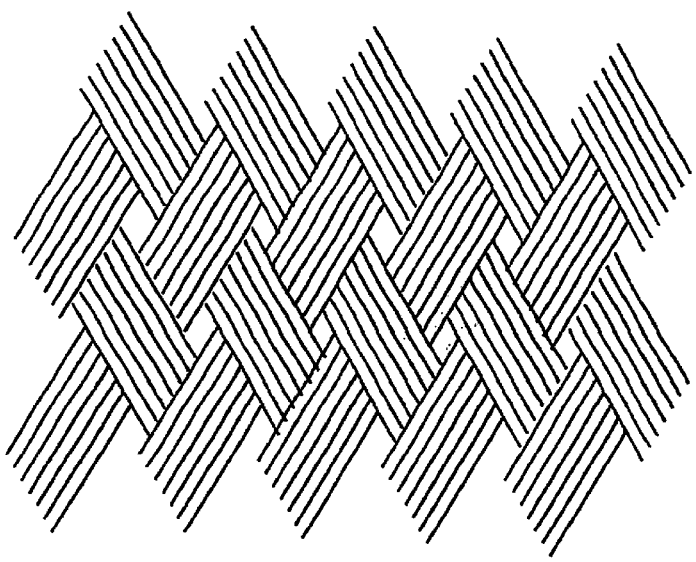
FIG. 18 is a view of the braid fibres or yarns at approximately 60 degrees from the horizontal axis across the bandage and approximately 30 degrees from the vertical axis across the bandage.

Referring to FIGS. 16, 17 and 18 the braid fibres or yarns are shown at different angles from the horizontal, or widthways, axis across the bandage and at different angles from the vertical, or lengthways, axis across the bandage.

When the tubular braided substrate is stretched lengthways the fibres will run along the lengthways direction at a smaller angle from the lengthways axis, as shown in FIG. 18, then when the tubular braided substrate is stretched widthways, as shown in FIG. 17.

Thus, the braided tubular structure as shown in FIG. 18 has greater lengthways strength than the braided tubular structure shown in FIG. 17. Accordingly, the braided tubular structure shown in FIG. 17 has greater widthways strength than the braided tubular structure shown in FIG. 18.

FIG. 16 shows a braided tubular structure whereby the lengthways and widthways strength are approximately equal.

What is claimed is:

1. A medical bandaging product adapted for being stored in a moisture-impervious package prior to use, comprising a moisture-curable hardening agent and a flexible, liquid-permeable braided fabric substrate defining a circumferential member with an open cross-section flattened so as to define two major, longitudinally-extended sides and two opposed, folded side edges.

2. A medical bandaging product according to claim 1, wherein said substrate is impregnated with said hardening agent.

3. A medical bandaging product according to claim 1, wherein said substrate is coated with said hardening agent.

4. A medical bandaging product according to claim 1, wherein said circumferential member is formed from length of flat braided material.

5. A medical bandaging product according to claim 1, wherein said circumferential member is formed from tubular braid.

6. A medical bandaging product according to claim 1, wherein said substrate further comprises a plurality of sets of fibers, wherein each of said sets is positioned at a 45 degree angle relative to at least one of the other sets.

7. A bandaging system, comprising a bandaging product including a moisture-curable agent impregnated into or coated onto a substrate, said bandaging product removably positioned within a moisture impervious container adapted for being resealed against entry of moisture after a desired length of the bandaging product has been removed from said container for use, wherein said substrate comprises a flexible, liquid permeable braided fabric substrate defining a circumferential member with an open cross-section flattened so as to define two major, longitudinally-extended sides and two opposed, folded side edges.

8. A bandaging system according to claim 7, wherein said container further comprises an enclosure formed of a moisture-impervious material and including an elongate dispensing sleeve adapted for being resealed to prevent moisture from entering said enclosure, said bandaging product being positioned in the enclosure for being dispensed in a desired use length from the sleeve.

9. A bandaging system according to claim 8, wherein said bandaging product further comprises a roll positioned within the enclosure and including a free end positioned in the dispensing sleeve in a single length along the length of the sleeve and sealed therein against entry of moisture until use.

* * * * *